(12) United States Patent
Pasin et al.

(10) Patent No.: US 8,961,680 B2
(45) Date of Patent: Feb. 24, 2015

(54) SOLVENT FORMULATIONS

(71) Applicant: TBF Environmental Technology Inc., Surrey (CA)

(72) Inventors: David Anthony Pasin, Vancouver (CA); Diego López-Arias, Vancouver (CA)

(73) Assignee: TBF Environmental Technology Inc. (CA)

( * ) Notice: Subject to any disclaimer, the term of this patent is extended or adjusted under 35 U.S.C. 154(b) by 0 days.

(21) Appl. No.: 14/172,578

(22) Filed: Feb. 4, 2014

(65) Prior Publication Data

US 2014/0255326 A1  Sep. 11, 2014

Related U.S. Application Data

(60) Provisional application No. 61/775,339, filed on Mar. 8, 2013.

(51) Int. Cl.
| | | |
|---|---|---|
| *B41M 5/165* | (2006.01) | |
| *A61Q 3/04* | (2006.01) | |
| *C09D 7/00* | (2006.01) | |
| *A61K 8/34* | (2006.01) | |
| *A61K 8/37* | (2006.01) | |
| *A61Q 3/02* | (2006.01) | |
| *C07C 33/22* | (2006.01) | |

(52) U.S. Cl.
CPC . *C09D 7/001* (2013.01); *A61K 8/34* (2013.01); *A61K 8/37* (2013.01); *A61Q 3/02* (2013.01); *A61Q 3/04* (2013.01); *C07C 33/22* (2013.01)
USPC .......................................... 106/311; 510/118

(58) Field of Classification Search
CPC ............... C09D 7/001; C07C 33/22
USPC .......................................... 106/311; 510/118
See application file for complete search history.

(56) References Cited

U.S. PATENT DOCUMENTS

| | | | |
|---|---|---|---|
| 5,449,474 A | 9/1995 | Lucas et al. | |
| 5,575,859 A | 11/1996 | Madsen et al. | |
| 5,746,836 A | 5/1998 | Fukai | |
| 6,040,284 A | 3/2000 | Marquis et al. | |
| 6,130,192 A | 10/2000 | Vitomir | |
| 6,187,108 B1 | 2/2001 | Machac, Jr. et al. | |
| 6,482,270 B1 | 11/2002 | Machac, Jr. et al. | |
| 6,720,008 B2 | 4/2004 | Allison | |
| 6,833,341 B2 | 12/2004 | Machac, Jr. et al. | |
| 6,994,799 B2 | 2/2006 | Van Driessche | |
| 7,674,760 B2 | 3/2010 | Hei et al. | |
| 2006/0281844 A1 | 12/2006 | Bortz | |
| 2010/0317560 A1 | 12/2010 | Ryther et al. | |
| 2012/0177999 A1 | 7/2012 | Im et al. | |
| 2014/0065432 A1 | 3/2014 | Wuerch et al. | |

FOREIGN PATENT DOCUMENTS

| | | |
|---|---|---|
| CA | 2331617 A1 | 11/1999 |
| CA | 2428588 A1 | 8/2002 |
| EP | 648820 A2 * | 4/1995 |
| EP | 0648820 A2 | 4/1995 |

OTHER PUBLICATIONS

Taylor, J. "Solvent Replacement for MEK in Parts Washing" (http://www.pprc.org/research/rapidresDocs/MEK_Replacement_RR_Draft.pdf), Aug. 2009.*
Begin, D.; Beaudry, C.; Gerin, M. "Cleaning of Paint Application Equipment with Propylene Carbonate and Benzyl Alcohol as Alternative to Butanone (MEK)" (http://www.subsport.eu/case-stories/310-en?lang=), Nov. 23, 2012.*
"SMC" "Dimethyl Carbonate (DMC) Replaces MEK" (http://www.subsport.eu/case-stories/310-en?lang=), Apr. 2011.*
Eastman Solvents Technical Tip, Suggested Replacements for MEK, Sep. 2006, Publication TT-33A, www.eastman.com/Literature_Center.
Elion, J.M., et al., Project Summary, Pollution Prevention Demonstration and Evaluation of Paint Application Equipment and Alternatives to Methylene Chloride and Methyl Ethyl Ketone, United States Environmental Protection Agency, Oct. 1996, EPA/600/SR-96/117.
International Search Report and Written Opinion mailed on May 30, 2014 for International Patent App. No. PCT/CA2014/050196 filed Mar. 7, 2014 (Applicants—TBF Environmental Technology, Inc.; Inventors—Pasin et al.; (11 pages).
Non-Final Office Action mailed on Sep. 10, 2014 for U.S. Appl. No. 14/316,835, filed Jun. 27, 2014 (Applicant—TBF Environmental Technology, Inc.; Inventor—Pasin et al.; (8 pages).

* cited by examiner

*Primary Examiner* — Sean Basquill
*Assistant Examiner* — Andrew S Rosenthal
(74) *Attorney, Agent, or Firm* — Ballard Spahr LLP

(57) ABSTRACT

The present disclosure provides, in part, a solvent composition including an an acetic acid alkyl ($C_1$-$C_4$) ester (e.g., methyl acetate (MA), ethyl acetate (EA), or tert-butyl acetate (TBAc)) and a carbonate ester (e.g., dimethyl carbonate, or propylene carbonate).

17 Claims, 3 Drawing Sheets

SOLVENT FORMULATIONS

FIELD OF INVENTION

The present disclosure relates generally to solvent formulations. More specifically, the present disclosure relates to solvent compositions that may be used to replace methyl ethyl ketone and/or acetone.

BACKGROUND OF THE INVENTION

Organic solvents, such as methyl ethyl ketone (MEK), acetone, xylene and toluene, and other hydrocarbons or oxygenated solvents are used in a number of applications. Many of these solvents have toxic and/or environmentally deleterious properties. For example, human and animal studies indicate that exposure to these chemicals can have detrimental effects on the central nervous system, as well as on the hepatic and renal systems. MEK and related ketones are considered carcinogenic and developmental toxins, can produce central nervous system effects, and show hepatic and renal toxicity (Raymond, 1991, Schwetz, 1995, Spencer 1976, Altenkirch, 1978); and acetone has been shown to enhance the toxicity of other chemicals through synergistic toxic effects (Hewitt 1983, Adams 1986, Freeman 1985). "Hazardous air pollutants" (or "HAPs"), also known as toxic air pollutants or air toxics, may cause cancer or other serious health effects, such as reproductive effects or birth defects, or adverse environmental and ecological effects. HAPs are regulated in many countries.

Furthermore, many organic solvents are highly volatile and, of the total amount released to the environment, a significant percentage eventually enters the atmosphere. As such, these solvents have been designated volatile organic compounds (or "VOCs") and are regulated. Compounds or solvents having lower volatility have been classified as VOC-exempt by many countries.

Methyl acetate is a carboxylate ester having the formula $CH_3COOCH_3$. It is a flammable liquid with a solubility of 25% in water at room temperature and is not stable in the presence of strong aqueous bases or aqueous acids. Methyl acetate is VOC exempt.

SUMMARY OF THE INVENTION

The present disclosure provides, in part, a solvent composition including an an acetic acid alkyl ($C_1$-$C_4$) ester (e.g., methyl acetate (MA), ethyl acetate (EA), or tert-butyl acetate (TBAc)) and a carbonate ester (e.g., dimethyl carbonate, or propylene carbonate).

In a first aspect, the disclosure provides a solvent composition including methyl acetate in an amount between about 65% v/v (or about 61.95 wt %) and about 80% v/v (or about 77.79 wt %); dimethyl carbonate in an amount between about 15% v/v (or about 16.76 wt %) and about 25% v/v; (or about 27.38 wt %) and benzyl alcohol in an amount between about 6.5% v/v (or about 7.06 wt %) and 10% v/v (or about 10.67 wt %).

In an alternative embodiment, the solvent composition may consist essentially of methyl acetate in an amount of about 72% v/v; dimethyl carbonate in an amount of about 20% v/v; and benzyl alcohol in an amount of about 8% v/v. In some embodiments, such as solvent composition may be used in dissolution and processing of acrylic polymers; the production of resins (such as acrylic resins, urethane resins, alkyd resins, phenolic resins, polyaspartic urethane resins, epoxy resins, saturated or unsaturated polyester resins); formulation or removal of nail polish (such as nitrocellulose-based nail polish, methacrylated monomer-based nail polish, oligonucleotide ("ligomer")-based nail polish, a UV cure nail polish or a LED cure nail polish); or fiberglass and/or gelcoat manufacturing; or waterproofing compounds.

In some embodiments, the flash point of the solvent composition may be at least −2° C. In an alternative embodiment, the flash point of the solvent composition may be about 0° C.

In some embodiments, the maximum incremental reactivity of the solvent composition may be no greater than 0.57. In an alternative embodiment, the maximum incremental reactivity of the solvent composition may be about 0.10.

In some embodiments, the evaporation rate of the solvent composition may be at least 1.4. In an alternative embodiment, the evaporation rate of the solvent composition may be about 3.62.

In some embodiments, the solvent composition may be substantially anhydrous.

In some embodiments, the solvent composition may be a low toxicity solvent composition.

In some embodiments, the solvent composition may be used as a methyl ethyl ketone and/or acetone replacement.

In some embodiments, the solvent composition may be used in paints, varnish, fiberglass and gelcoat manufacturing, paint and varnish removers, coatings, inks, adhesives, hard surface cleaners, household dyes, tints, insecticides, laundry starches, lubricating greases and oils, automotive chemicals, markers, nail polish and polish remover, shoe polish, undercoats, waterproofing compounds, particleboard, surface preparation, general and heavy duty degreasing, laboratory and equipment wipe solvent, general purpose surface wipe cleaner and/or paint gun and paint line cleaner.

In another aspect, the disclosure provides a method of making a MEK or acetone replacement composition by providing methyl acetate in an amount between about 65% v/v (or about 61.95 wt %) and about 80% v/v (or about 77.79 wt %); dimethyl carbonate in an amount between about 15% v/v (or about 16.76 wt %) and about 25% v/v; (or about 27.38 wt %) and benzyl alcohol in an amount between about 6.5% v/v (or about 7.06 wt %) and 10% v/v (or about 10.67 wt %); and combining the methyl acetate, dimethyl carbonate and benzyl alcohol to form a homogeneous blend.

In another aspect, the disclosure provides a kit include a solvent composition as described herein together with instructions for use as a MEK or acetone replacement.

Other aspects and features of the present disclosure will become apparent to those ordinarily skilled in the art upon review of the following description of specific examples in conjunction with the accompanying figures.

BRIEF DESCRIPTION OF THE DRAWINGS

These and other features of the invention will become more apparent from the following description in which reference is made to the appended drawings wherein.

DETAILED DESCRIPTION

Figure 1:
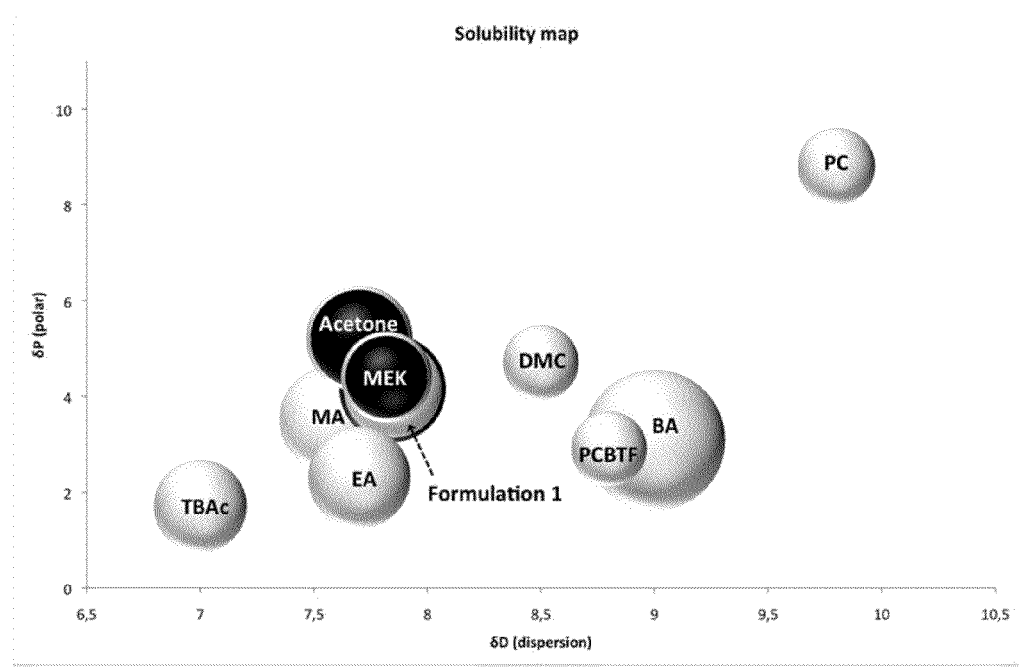
FIG. 1 is a representation of the different components of the Hansen Solubility Parameters: Dispersion, Polar and Hydrogen bonding for various solvents. The size of the spheres correspond to the hydrogen bonding component.

The present disclosure provides, in part, a solvent composition including an acetic acid alkyl (C1-C4) ester (referred to herein as "acetate ester"), such as methyl acetate (MA), ethyl acetate (EA), or tert-butyl acetate (TBAc)) and a carbonate ester (e.g., dimethyl carbonate (DMC), or propylene carbonate (PC)).

By "acetate ester," as used herein, is meant an acetic acid alkyl ($C_1$-$C_4$) ester having the formula $CH_3CO_2R$, where R is $C_1$-$C_4$ alkyl. "Alkyl" refers to a straight or branched hydrocarbon chain group consisting solely of carbon and hydrogen atoms, containing no unsaturation and including, for example, from one to four carbon atoms, such as 1, 2, 3, or 4 carbon atoms.

In some embodiments, the acetate ester may be present in the solvent composition in any amount between about 40% v/v to about 95% v/v, or 65% v/v to about 95% v/v, or any amount between about 65% v/v to about 70% v/v, or any amount between about 70% v/v to about 75% v/v, or any amount between about 75% v/v to about 80% v/v, or any amount between about 80% v/v to about 85% v/v, or any amount between about 85% v/v to about 90% v/v, or any amount between about 90% v/v to about 95% v/v, or any value in between, for example, 40%, 45%, 50%, 55%, 60%, 65%, 70% v/v, 75% v/v, 80% v/v, 85% v/v, 90%, 95% v/v, etc.

In some embodiments, the acetate ester may be MA, which may be present in the solvent composition in any amount between about 40% v/v to about 95% v/v, or any amount between about 60% v/v or 65% v/v to about 95% v/v, or any amount between about 65% v/v to about 70% v/v, or any amount between about 70% v/v to about 75% v/v, or any amount between about 75% v/v to about 80% v/v, or any amount between about 80% v/v to about 85% v/v, or any amount between about 85% v/v to about 90% v/v, or any amount between about 90% v/v to about 95% v/v, or any value in between, for example, 70% v/v, 75% v/v, 80% v/v, 85% v/v, 90% v/v, etc.

In some embodiments, the acetate ester may be EA, which may be present in the solvent composition in any amount between about 40% v/v to about 95% v/v, or any amount between about 65% v/v to about 95% v/v, or any amount between about 65% v/v to about 70% v/v, or any amount between about 70% v/v to about 75% v/v, or any amount between about 75% v/v to about 80% v/v, or any amount between about 80% v/v to about 85% v/v, or any amount between about 85% v/v to about 90% v/v, or any amount between about 90% v/v to about 95% v/v, or any value in between, for example, 70% v/v, 75% v/v, 80% v/v, 85% v/v, 90% v/v, etc.

In some embodiments, the acetate ester may be TBAc, which may be present in the solvent composition in any amount between about 40% v/v to about 95% v/v, or any amount between about 65% v/v to about 95% v/v, or any amount between about 65% v/v to about 70% v/v, or any amount between about 70% v/v to about 75% v/v, or any amount between about 75% v/v to about 80% v/v, or any amount between about 80% v/v to about 85% v/v, or any amount between about 85% v/v to about 90% v/v, or any amount between about 90% v/v to about 95% v/v, or any value in between, for example, 70% v/v, 75% v/v, 80% v/v, 85% v/v, 90% v/v, etc.

In some embodiments, the carbonate ester may be present in the solvent composition in any amount between about 5% v/v to about 55% v/v, or any amount between about 5% v/v to about 35% v/v, in any amount between about 10% v/v to about 30% v/v, or any value in between, for example, 10% v/v, 15% v/v, 20% v/v, 25% v/v, 30% v/v, 40% v/v, 45% v/v, etc.

In some embodiments, the carbonate ester may be PC, which may be present in the solvent composition in any amount between about 5% v/v to about 35% v/v, or in any amount between about 10% v/v to about 30% v/v, or any value in between, for example, 10% v/v, 11% v/v, 12% v/v, 13% v/v, 14% v/v, 15% v/v, 20% v/v, 25% v/v, 30% v/v, etc.

In some embodiments, the carbonate ester may be DMC, which may be present in the solvent composition in any amount between about 5% v/v to about 55% v/v, or in any amount between about 10% v/v to about 30% v/v, or any value in between, for example, 10% v/v, 15% v/v, 20% v/v, 25% v/v, 30% v/v, 40% v/v, 45% v/v, 52% v/v, etc.

In further embodiments, the solvent composition may additionally include a non-toxic or low-toxicity benzene-containing compound, such as benzyl alcohol (BA) or parachlorobenzotrifluoride (PCBTF). In some embodiments, the benzyl alcohol (BA) or parachlorobenzotrifluoride (PCBTF) may be in an amount between about 5% v/v and about 15% v/v, or any value in between, for example, 5% v/v, 6% v/v, 7% v/v, 8% v/v, 9% v/v, 10% v/v, 11% v/v, 12% v/v, 13% v/v, 14% v/v, 15% v/v, etc.

In some embodiments, a solvent composition according to the present disclosure includes methyl acetate in an amount between about 65% v/v (about 58.95 wt %) and about 95% v/v (about 93.63 wt %) and propylene carbonate in an amount between about 5% v/v (6.37 wt %) and about 35% v/v (41.04 wt %).

In some embodiments, a solvent composition according to the present disclosure includes about 88% v/v (about 85.01 wt %) methyl acetate and about 12% v/v (about 14.99 wt %) polypropylene carbonate.

In some embodiments, a solvent composition according to the present disclosure includes about 70% v/v (about 64.34 wt %) methyl acetate and about 30% v/v (about 35.65 wt %) polypropylene carbonate.

In some embodiments, a solvent composition according to the present disclosure includes methyl acetate in an amount between about 60% v/v (about 56.78 wt %) and about 85% v/v (about 83.25 wt %), dimethyl carbonate in an amount between about 10% v/v (about 11.25 wt %) and about 30% v/v (about 32.62 wt %) and benzyl alcohol in an amount between about 5% v/v (about 5.48 wt %) and about 10% v/v (about 10.6 wt %).

In some embodiments, a solvent composition according to the present disclosure includes about 72% v/v (about 69.27 wt %) methyl acetate, about 20% v/v (22.11 wt %) dimethyl carbonate, and about 8% (about 8.62 wt %) benzyl alcohol.

In some embodiments, a solvent composition according to the present disclosure includes methyl acetate in an amount between about 65% v/v (or about 61.95 wt %) and about 80% v/v (or about 77.79 wt %); dimethyl carbonate in an amount between about 15% v/v (or about 16.76 wt %) and about 25% v/v; (or about 27.38 wt %) and benzyl alcohol in an amount between about 6.5% v/v (or about 7.06 wt %) and 10% v/v (or about 10.67 wt %).

In some embodiments, a solvent composition according to the present disclosure includes methyl acetate in an amount between about 65% v/v (or about 61.95 wt %) and about 78.5% v/v (or about 76.20 wt %); dimethyl carbonate in an amount between about 15% v/v (or about 16.76 wt %) and about 25% v/v; (or about 27.38 wt %) and benzyl alcohol in an amount between about 6.5% v/v (or about 7.06 wt %) and about 10% v/v (or about 10.67 wt %).

It is to be understood that varying the concentration of a reagent in a composition will generally require a corresponding adjustment (increase or decrease) in the amount of the other reagents in the composition.

In some embodiments, a solvent composition according to the present disclosure includes an acetate ester, such as MA, EA, or TBAc, in combination with additional reagents to increase dispersion and decrease hydrogen bonding and/or to decrease the polarity of the composition. For example, a solvent composition that resembles the behaviour of MEK or acetone as a solvent may be formulated using mathematical models to predict the solubility profile of solvent blends. Accordingly, in some embodiments, a solvent composition according to the present disclosure may be formulated according to Hansen solubility parameters (HSP) (Hansen, 1999) and may have: a dispersion parameter ($\delta D$) between about 7.7 and about 8.5; a polarity parameter ($\delta P$) between about 4 and about 5.2; and a hydrogen bonding parameter ($\delta H$) between about 3.0 and about 3.6. Such parameters result in a Hansen Solubility Parameter ($\delta$ MPa) of about 9.0 to about 10.4, where $\delta^2 = \delta D^2 + \delta P^2 + \delta H^2$. Accordingly, in some embodiments, a solvent composition according to the present disclosure may have a dispersion parameter higher than that of MA (7.58). In some embodiments, a solvent composition according to the present disclosure includes a composition with HSP values similar to those of MEK. In some embodiments, a solvent composition according to the present disclosure includes a composition in which $\delta P$ and $\delta H$ values are similar to those of MEK.

In alternative embodiments, a solvent composition according to the present disclosure may have: a dispersion parameter ($\delta D$) between about 7.5 and about 8; a polarity parameter ($\delta P$) between about 3 and about 4; and a hydrogen bonding parameter ($\delta H$) between about 3.2 and about 4. Such parameters result in a Hansen Solubility Parameter ($\delta$ MPa) of about 8.68 to about 9.79, where $\delta^2 = \delta D^2 + \delta P^2 + \delta H^2$. In some embodiments, a solvent composition according to the present disclosure includes a composition with HSP values similar to those of acetone. In some embodiments, a solvent composition according to the present disclosure includes a composition in which $\delta P$ and $\delta H$ values are similar to those of acetone.

Table 1 shows the Hansen Solubility Parameters for various compounds and compositions and FIG. 1 shows a three-dimensional representation of many of these compounds.

TABLE 1

Hansen Solubility parameters of blends, single components, MEK and acetone $\delta^2 = \delta D^2 + \delta P^2 + \delta H^2$
1 hildebrand = 1 cal1/2 cm-3/2 = 0.48888 MPa1/2
(IS) = 2.4542*10$^{-2}$ kcal/mol 1/2 A$^{-3/2}$

|   | $\delta$ (MPa) | $\delta D$ (dispersion) | $\delta P$ (polarity) | $\delta H$ (hydrogen bonding) |
|---|---|---|---|---|
| PC | 13.32216199 | 9.8 | 8.8 | 2 |
| PCBTF |  | 8.8 | 2.9 | 1.9 |
| DMC | 9.896969233 | 8.5 | 4.7 | 1.9 |
| TBA | 7.765307463 | 7 | 1.7 | 2.9 |
| Ethyl acetate | 8.8 | 7.7 | 2.3 | 3.5 |
| Methyl acetate | 9.147961522 | 7.58 | 3.52 | 3.72 |
| Formulation 1 | 9.435396725 | 7.896 | 3.7444 | 3.558 |
| Formulation 2 | 9.547972082 | 7.8464 | 4.1536 | 3.5136 |
| Formulation 3 | 10.25238566 | 8.2682 | 5.1568 | 3.1868 |
| MEK | 9.1 | 7.82 | 4.4 | 2.49 |
| Acetone | 9.928746144 | 7.7 | 5.2 | 3.5 |

In some embodiments, the carbonate ester may be used to increase the dispersion and decrease the hydrogen bonding of the composition. Without being bound to any particular theory, the carbonate ester may be used to modify the solubility and solvency parameters of the acetate ester to, for example and adjust the evaporation rate to that approximating MEK.

In some embodiments, the benzene-containing compound, such as benzyl alcohol, may be used to decrease the polarity of the composition. In alternative embodiments the benzene-containing compound, such as benzyl alcohol, may be used to improve the capacity of the composition to, for example, remove/dissolve epoxy based coatings.

In some embodiments, a solvent composition according to the present disclosure may include reagents that are not classified as hazardous air pollutants (HAPs), as environmentally hazardous, or as ozone-depleting (VOCs). In some embodiments, a solvent composition according to the present disclosure may include reagents declared exempt by the National Pollutant Release Inventory (NPRI).

In some embodiments, a solvent composition according to the present disclosure may include compounds or reagents that are VOC-exempt. By "VOC-exempt" is meant a compound or reagent that has reduced photochemical reactivity (i.e., does not contribute to ozone formation) and has been classified as such by at least one governmental agency, such as the Environmental Protection Agency (EPA) of the United States of America or Environment Canada. Such compositions are useful in reducing VOC emissions. MA and PCBTF are presently VOC-exempt.

A compound's maximum incremental reactivity (MIR) value is a measure of the compound's ability to generate ozone due to photochemical degradation. The lower the MIR value, the less ozone (and, accordingly, the less smog) that is generated by the compound. In some embodiments, a solvent composition according to the present disclosure may have a MIR value lower than acetone (MIR 0.43) or MEK (MIR 1.49), or both. In alternative embodiments, compositions according to the present disclosure may have a MIR value similar to methyl acetate (MIR 0.07). In some embodiments, compositions with low MIR values are useful in aerosol or coating applications. Compositions according to the present disclosure that have suitably low MIR values can, in some embodiments, be mixed with aerosol and coating formulations. The MIR values of the resultant mixtures can be calculated and assessed for their ability to meet reactivity standards, such as those established by the Environmental Protection Agency (EPA) of the U.S.A.

In some embodiments, a solvent composition according to the present disclosure may have low volatility (or high flash point).

In some embodiments, a solvent composition according to the present disclosure has a higher flash point than acetone (−20° C.) or MEK (−9° C.) or MA (−4° C.). In some embodiments, a solvent composition according to the present disclosure has a flash point of greater than 0° C., as determined by, for example, Catoire, 2006. In some embodiments, a solvent composition according to the present disclosure has a flash point of greater than 5° C., as determined by, for example, Catoire, 2006. In some embodiments, a solvent composition according to the present disclosure has a flash point of greater than 37° C., as determined by, for example, Catoire, 2006. In some embodiments, compositions with a flash point value of greater than 37° C. are considered non-flammable and are therefore useful in applications where flammability is a concern although solvent compositions with lower flash points may be used for a variety of industrial applications.

In some embodiments, a solvent composition according to the present disclosure may have low toxicity as determined, for example by one or more of oral LD50 on rats, biodegradability, teratogenicity, carcinogenicity and/or hepatic and renal toxicity measurements, which can be determined using standard methods. In some embodiments, a solvent composition according to the present disclosure may contain reagents classified as non-carcinogenic.

In some embodiments, a solvent composition according to the present disclosure may not contain substantial amounts of benzene ($C_6H_6$). In some embodiments, a solvent composition according to the present disclosure may be substantially free of benzene.

In some embodiments, a solvent composition according to the present disclosure may have an evaporation rate approximating that of MEK at ambient or room temperatures. Evaporation rates can be expressed relative to the evaporation of n-butyl acetate (=1), as a standard. In alternative embodiments, a solvent composition according to the present disclosure may have an evaporation rate about 1, 1.5 or 2 times faster than MEK at ambient or room temperatures.

In some embodiments, a solvent composition according to the present disclosure does not leave a residue after evaporation to dryness at, for example, ambient or room temperature.

In some embodiments, a solvent composition according to the present disclosure may be substantially anhydrous, for example, containing less than 0.02 wt % water. In alternative embodiments, a solvent composition according to the present disclosure may contain less than 550 ppm of water.

In some embodiments, a solvent composition according to the present disclosure may be substantially immiscible with water.

In some embodiments, a solvent composition according to the present disclosure has a purity of, for example, at least 99.5%, for example, at least 99.6%, 99.7%, 99.8%, 99.9%, or 100%. In alternative embodiments, the acetate ester (such as MA, EA or TBAc), may have a purity of, for example, at least 99.5%. In alternative embodiments, the carbonate ester, may have a purity of, for example, at least 99.5%.

In some embodiments, a solvent composition according to the present disclosure may be biodegradable. For example, in some embodiments, solvent compositions according to the present disclosure may be readily biodegradable to $CO_2$ and water.

In some embodiments, a solvent composition according to the present disclosure may have a high loading capacity, as determined for example by measurements of peak widths at differing loading levels.

In some embodiments, a solvent composition according to the present disclosure may have improved flow characteristics, for example, when compared to and/or acetone.

In some embodiments, a solvent composition according to the present disclosure may have low viscosity. For example, a solvent composition according to the present disclosure can be 10-25% more efficient in viscosity reduction than and/or acetone.

In some embodiments, a solvent composition according to the present disclosure may have improved solvency, relative to for example, MEK and/or acetone. This may, in some embodiments, permit the use of less solvent when compared to compositions containing MEK and/or acetone. In some embodiments, solvent compositions according to the present disclosure may have a solvency approximating that of MEK and/or acetone.

In some embodiments, a solvent composition according to the present disclosure may have a specific gravity of about 0.96 g/ml.

In some embodiments, a solvent composition according to the present disclosure may have performance characteristics approximating that of MEK and/or acetone, as described herein or known in the art.

In some embodiments, a solvent composition according to the present disclosure may be recycled through distillation at an appropriate temperature (for example, above the boiling point of 70° C. (158° F.).

In some embodiments, a solvent composition according to the present disclosure may have a mild odor. In some embodiments, compositions according to the present disclosure may include reagents that do not have an unpleasant and/or strong odor.

In some embodiments, a solvent composition according to the present disclosure may be useful in replacing MEK or MEK blends. The compositions can be used, for example, as a solvent in various applications. Examples of contemplated applications include, without limitation: reformulation of an aerosol to meet a reactivity limit while maintaining performance properties and reducing the formation of tropospheric ozone; dissolution of a resin; use as a paint thinner; use as a paint remover; use as a cleaner; use as a degreaser; and use an adhesive remover.

In some embodiments, a solvent composition according to the present disclosure may be useful in the manufacturing and formulation of paints, coatings, polymers, inks, adhesives, personal care products, as well as in industrial, commercial cleaning/de-greasing applications.

In some embodiments, a solvent composition according to the present disclosure may be useful in paints and coating formulations and/or cleaning, paint and/or varnish removers, ink and/or marker formulations and/or cleaning, adhesive formulations and/or cleaning and/or removal, gelcoat formulations and/or cleaning, fiberglass manufacturing, hard surface cleaners, undercoat formulation and/or cleaning, waterproofing compounds, household dyes and/or tints, laundry starches and shoe polishes, nail polish and/or nail polish removers, general aerospace cleaning, lubricating oils and/or greases, automotive chemicals and cleaners, etc.

In some embodiments, a solvent composition according to the present disclosure may be useful as a surface preparation and/or precision cleaner, general purpose surface wipe cleaner (for example, prior to painting), general and/or heavy duty degreaser, laboratory and equipment wipe solvent, brake and/or contact cleaner, paint gun and paint line cleaner, etc.

In some embodiments, a solvent composition according to the present disclosure may be useful as a chemical intermediate, a dewaxing agent in for example lubricant base oil production, etc.

In some embodiments, a solvent composition according to the present disclosure may be useful in the production and cleaning of magnetic tapes, In some embodiments, a solvent composition according to the present disclosure may be useful as a solvent for fats, oils, waxes, etc.

In some embodiments, a solvent composition according to the present disclosure may be useful in the formulation and production of resins.

In some embodiments, a solvent composition according to the present disclosure may be useful in the formulation of high solids coatings, which may for example, be useful in reducing emissions from coating operations.

In some embodiments, a solvent composition according to the present disclosure may be useful as a diluents in the production of lacquers for automotive/furniture finishes, adhesives for PVC pipes, resin thinners and clean-up operations, reaction/extraction solvent for pharmaceuticals, etc.

In some embodiments, a solvent composition according to the present disclosure may be useful in the production of cyanoacrylate adhesives. In alternative embodiments, a solvent composition according to the present disclosure may be useful to remove cyanoacrylate adhesives from a variety of surfaces, substrates, human tissue or skin, etc.

In some embodiments, a solvent composition according to the present disclosure may be useful in the production of cosmetics, included but not limited to perfumes and/or nail polish, such as nitrocellulose-based nail polish, methylacrylated monomer-based nail polish, oligonucleotide ("ligomer")-based nail polish, etc. In alternative embodiments, a solvent composition according to the present disclosure may be useful to remove these types of nail polish and/or leave the nail bed stain and residue-free as well as prepare the nail for the application of any of the above nail polishes.

In some embodiments, the compositions do not cause paints to curdle or leave an oily residue after evaporation.

In some embodiments, Formulation 1 may be used in dissolution and processing of acrylic polymers.

In some embodiments, Formulation 1 may be used in the production of resins, such as acrylic resins, urethane resins, alkyd resins, phenolic resins, polyaspartic urethane resins, epoxy resins, saturated and/or unsaturated polyester resins, etc.

In some embodiments, Formulation 1 may be used in formulation or removal of nail polish, such as nitrocellulose-based nail polish, methacrylated monomer-based nail polish, oligonucleotide ("ligomer")-based nail polish, etc. In some embodiments, Formulation 1 may be used in UV cure and/or LED cure nail polish.

In some embodiments, Formulation 1 may be used in fiberglass and/or gelcoat manufacturing.

In some embodiments, Formulation 1 may be used in may be used in waterproofing compounds.

In some embodiments, Formulation 1 may be used as a replacement for MEK in epoxy formulas.

In some embodiments, Formulation 1 may be used to replace MEK in 2K polyurethane formulas if it contains no hydroxol groups capable of reacting with isocyanate cross-linkers and if the water content is below 500 ppm. In some embodiments, Formulation 1 may be used in 2 k polyurethane systems in either the polyol and/or isocyanate portions of the system.

In some embodiments, Formulation 9 may be used as a replacement for MEK and/or acetone in, for example, cleaning or other applications. In some embodiments, Formulation 9 may be used as a replacement for MEK and/or acetone in precision cleaning applications, cleaning hard surfaces and/or general cleaning and degreasing.

In some embodiments, Formulation 9 may be useful in aerospace cleaning applications.

In some embodiments, Formulation 9 may be useful in preparing surfaces prior to painting, due to its ability to evaporate quickly and leave no or minimal surface residue.

In some embodiments, Formulation 9 may be useful in or to: clean and/or remove wax, paint, varnish and/or coatings, clean fiberglass, clean gelcoat, clean and/or remove inks and/or markers, clean and/or remove dyes, clean excess oils and/or grease, clean nail polish, clean shoe polish, clean brakes and/or contacts, clean and/or remove adhesives.

In alternative embodiments, Formulation 9 is not used in the preparation of formulations.

It is to be understood that a solvent composition according to the present disclosure can be used in a variety of applications in which MEK and/or acetone is traditionally used, and can be used to replace the MEK and/or acetone in such applications.

EXAMPLE 1

Candidate compounds were selected using a number of environmental criteria, such as low flammability, safety, low VOC or VOC exempt status, and sustainable sourcing.

Candidate compounds were also selected based on their physicochemical properties as, for example, determined from various chemical databases, such as CHEMnetBASE or Chemspider. Candidates with relatively high flash points, low toxicity and low vapor pressures, when compared with MEK, acetone, n-methyl pirrolidine (NMP) and methyl n-propyl ketone (MPK), etc. were selected for further testing.

The selected compounds were subsequently combined in different initial blends (Table 2). The blends or formulations described herein were selected through standardized performance tests on fresh and cured epoxy and urethane resins and MEK-based paints. Double blinded standardized performance tests were conducted to identify blends for further testing. The capacity of the blends to properly dissolve 2 adhesives, three epoxy-based coatings and one MEK-based paint was assessed on fresh and cured samples. The odor of the blends was also tested.

TABLE 2

|  | Propylene carbonate | d-limonene | Tripropylene glyco methy ether | Benzyl alcohol | Ethyl acetate | Methyl acetate | Methy n-amil ketone | Methy n-propyl ketone | Dimethyl carbonate |
|---|---|---|---|---|---|---|---|---|---|
| 1 | 40 | 0 | 60 | | | | | | |
| 2 | 60 | | | 40 | | | | | |
| 3 | 40 | | | 60 | | | | | |
| 4 | | | | | 60 | | | 40 | |
| 5 | | | | | | 60 | | 40 | |
| 6 | | | | | | 60 | 40 | | |
| 7 | | | | | 60 | | 40 | | |
| 8 | 40 | | 20 | | | | | | 40 |
| 9 | 60 | | | 20 | | | | | 20 |
| 10 | 20 | | | 20 | | | | | 60 |
| 11 | | | | | | | 20 | | 80 |
| 12 | | | | | | | 40 | | 60 |
| 13 | | | | | | | | 20 | 80 |
| 14 | | | | | | | | 40 | 60 |
| 15 | | | | | 20 | | | | 80 |
| 16 | | | | | 40 | | | | 60 |
| 17 | 20 | | | | | | | | 80 |
| 18 | 40 | | | | | | | | 60 |
| 19 | | | | 30 | | | | 70 | |
| 20 | | | | 30 | | 70 | | | |
| 21 | | | | 30 | | | | 30 | 40 |
| A | | | | 10 | 50 | | | | 40 |

TABLE 2-continued

|   | Propylene carbonate | d-limonene | Tripropylene glyco methy ether | Benzyl alcohol | Ethyl acetate | Methyl acetate | Methy n-amil ketone | Methy n-propyl ketone | Dimethyl carbonate |
|---|---|---|---|---|---|---|---|---|---|
| B |  |  |  | 20 |  |  |  | 15 | 65 |
| C (Formulation 3) | 30 |  |  |  |  | 70 |  |  |  |
| D |  |  |  | 10 | 90 |  |  |  |  |
| E (Formulation 2) | 12 |  |  |  |  | 88 |  |  |  |
| F (Formulation 1) |  |  |  | 8 |  | 72 |  |  | 20 |

Figure 2:
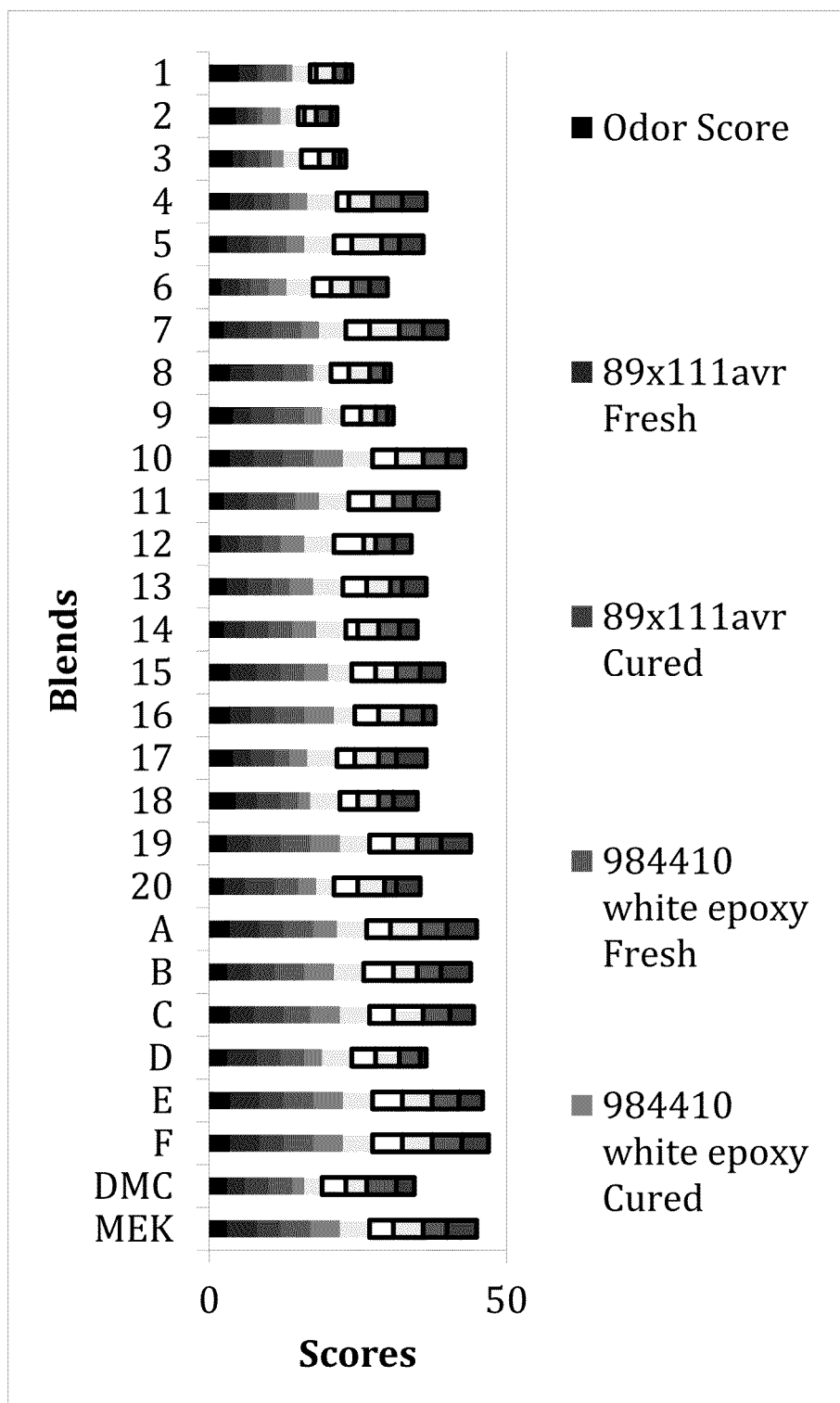
FIG. 2 shows initial blends from 1 to 20. Blends A, E and F correspond to Formulations 1, 3 and 2 respectively.

Blends were also tested as cleaners, paint removers, degreasers and adhesive removers. (FIG. 2).

Blends 3 and 4 were discarded due to their poor performance in these tests. Blends C, E and F correspond to Formulations 3, 2, and 1, respectively, as described herein.

EXAMPLE 2

A solvent composition (Formulation 1) was prepared by mixing the following:
72% (v/v) or 69.27 wt % methyl acetate ≥99% purity (CAS #79-20-9)
20% (v/v) or 22.11 wt % dimethyl carbonate ≥99.50% (CAS #616-38-6)
8% (v/v) or 8.62% wt % benzyl alcohol, ≥99.90% purity (CAS #100-51-6)

In Formulation 1, dimethyl carbonate was used to increase the dispersion and decrease the hydrogen bonding of the blend, while benzyl alcohol was used to lower the polarity.

Formulation 1 has a MIR value of 0.46 and a predicted flash point of about 7.5° C.

Formulation 1 has an evaporation rate=3.6 (MEK=3.8).

EXAMPLE 3

A solvent composition (Formulation 2) was prepared by mixing the following:
88% (v/v) or 85.01 wt % methyl acetate ≥99% purity (CAS #79-20-9)
12% (v/v) or 14.99 wt % propylene carbonate ≥99.5% purity (CAS #108-32-7)

Formulation 2 has an MIR value of 0.09 and a predicted flash point of about 9° C.

Formulation 2 was able to dissolve MEK-based paints and resins successfully.

EXAMPLE 4

A solvent composition (Formulation 3) was prepared by mixing the following:
70% (v/v) or 64.34 wt % methyl acetate ≥99% purity (CAS #79-20-9)
30% (v/v) or 35.65 wt % propylene carbonate ≥99.5% purity (CAS #108-32-7)

Formulation 3 has a MIR value of 0.12, and a flash point of about 39° C. (<37° C.).

EXAMPLE 5

A solvent composition (Formulation 4) was prepared by mixing the following:
88% (v/v) or 85.01 wt % ethyl acetate
12% (v/v) or 14.99 wt % propylene carbonate

EXAMPLE 6

A solvent composition (Formulation 5) was prepared by mixing the following:
40% (v/v) or 35.12 wt % tert-butyl acetate
52% (v/v) or 56.42 wt % dimethyl carbonate
8% (v/v) or 8.46 wt % benzyl alcohol

EXAMPLE 7

A solvent composition (Formulation 6) was prepared by mixing the following:
65% (v/v) or 57.18 wt % tert-butyl acetate
35% (v/v) or 42.82 wt % propylene carbonate

EXAMPLE 8

A solvent composition (Formulation 7) was prepared by mixing the following:
55% (v/v) or 46.78 wt % tert-butyl acetate
45% (v/v) or 53.22 wt % propylene carbonate

EXAMPLE 7

A solvent composition (Formulation 8) was prepared by mixing the following:
75% (v/v) or 68.33 wt % tert-butyl acetate
25% (v/v) or 31.67 wt % propylene carbonate

EXAMPLE 8

A solvent composition (Formulation 9) was prepared by mixing the following:
75% or 72.30 wt % Methyl Acetate
25% or 27.69 wt % Dimethyl Carbonate Formulation 9 has a predicted flash point of about 7° C. to about 10° C.

EXAMPLE 9

Figure 3:
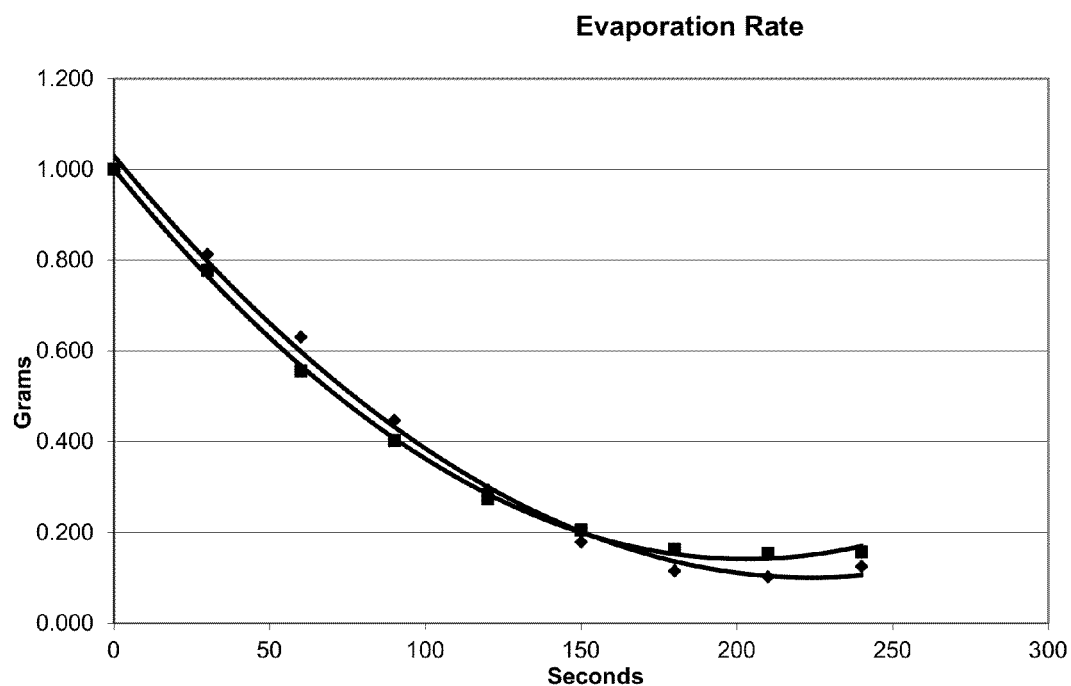
FIG. 3 is a graph comparing the evaporation rate of Formulation 1 (squares) with that of MEK (diamonds).

Formulation 1 was evaluated as a replacement for MEK in an epoxy-polyamide clear formulation. The evaporation rate of Formulation 1 was compared with MEK, MIBK and Butyl Acetate, as shown in FIGS. 3A-B.

Two epoxy clear formulas were prepared as follows:

|  | 32031-1 | 32031-2 |
|---|---|---|
| Part A | | |
| DER 662 Solid Epoxy Resin | 438.92 | 438.92 |
| Xylene | 146.31 | 146.30 |
| Methyl Ethyl Ketone | 292.61 | |
| Formulation 1 | | 292.62 |
| Total | 877.84 | 877.84 |
| Part B | | |
| Ancamide 2060 Polyamide | 101.29 | 99.30 |
| Weight Solids, % | 55.17 | 55.17 |
| Volume Solids, % | 46.81 | 49.85 |
| Specific Gravity | 0.979 | 1.043 |
| Viscosity: Part A | 50.6 KU | 52.7 KU |
| Mixed Viscosity: | 52.1 KU | 55.3 KU |

Formulation 1 was found to have a lower, milder odor compared to MEK. The evaporation rate of Formulation 1 was 4.17, which is similar to the published MEK ER 4.0. In the epoxy formula tested, Formulation 1 has slightly less solvent power than MEK. Substitution of the MEK with Formulation 1 resulted in a minor 2-3 KU increase in viscosity.

REFERENCES

Adams, N., Goulding, K. H. & Dobbs, A. J. (1986). Effect of acetone on the toxicity of four chemicals to *Selenastrum capricornutum*. Bull. Environ. Contam. Toxicol., 36, 254-9.

Freeman J J, Hayes E P. (1985) Acetone potentiation of acute acetonitrile toxicity in rats. Journal of Toxicology and Environmental Health 15:609-621.

Hewitt, W. R., and Plaa, G. L. (1983). Dose dependent modification of 1,1-dichloroethylene toxicity by acetone. Toxicol. Lett. 16, 145-152.

Catoire, L., Paulmier, S., (2006) Estimation of closed cup flash points of combustible solvent blends. Journal of Physical and Chemical Reference Data 35, 9-14.

C. M. Hansen, (1999) 'Hansen Solubility Parameters: A User's Handbook'. CRC Press LLC, New York.

Raymond, P., & Plaa, G. L. (1995). Ketone potentiation of haloalkane induced hepato and nephrotoxicity. II. implication of monooxygenases. *Journal of Toxicology and Environmental Health, Part A Current Issues*, 46(3), 317-328.

Schwetz, B. A., Mast, T. J., Weigel, R. J., Dill, J. A., & Morrissey, R. E. (1991). Developmental toxicity of inhaled methyl ethyl ketone in Swiss mice. *Fundamental and applied toxicology*, 16(4), 742-748.

Spencer, P. S., & Schaumburg, H. H. (1976). Feline nervous system response to chronic intoxication with commercial grades of methyl*n*-butyl ketone, methyl*iso*butyl ketone, and methyl ethyl ketone. *Toxicology and Applied Pharmacology*, 37(2), 301-311.

Altenkirch, H., Stoltenburg, G., & Wagner, H. M. (1978). Experimental studies on hydrocarbon neuropathies induced by methyl-ethyl-ketone (MEK). *Journal of neurology*, 219(3), 159-170.

All citations are hereby incorporated by reference.

In the preceding description, for purposes of explanation, numerous details are set forth in order to provide a thorough understanding of the examples. However, it will be apparent to one skilled in the art that these specific details are not required.

The above-described examples are intended to be exemplary only. Alterations, modifications and variations can be effected to the particular examples by those of skill in the art without departing from the scope, which is defined solely by the claims appended hereto.

What is claimed is:

1. A solvent composition comprising:
   (a) methyl acetate in an amount between about 65% v/v and about 85% v/v;
   (b) dimethyl carbonate in an amount between about 10% v/v and about 25% v/v; and
   (c) benzyl alcohol in an amount between about 6.5% v/v and 12% v/v.

2. The solvent composition of claim 1 consisting essentially of:
   (a) methyl acetate in an amount of about 72% v/v;
   (b) dimethyl carbonate in an amount of about 20% v/v; and
   (c) benzyl alcohol in an amount of about 8% v/v.

3. The solvent composition of claim 1, wherein the flash point of the solvent composition is at least −2° C.

4. The solvent composition of claim 1, wherein the flash point of the solvent composition is about 0° C.

5. The solvent composition of claim 1, wherein the maximum incremental reactivity of the solvent composition is no greater than 0.57.

6. The solvent composition of claim 1, wherein the maximum incremental reactivity of the solvent composition is about 0.10.

7. The solvent composition of claim 1, wherein the evaporation rate of the solvent composition is at least 1.4.

8. The solvent composition of claim 1, wherein the evaporation rate of the solvent composition is about 3.62.

9. The solvent composition of claim 1, wherein the solvent composition is substantially anhydrous.

10. A product, comprising:
    the solvent composition of claim 1,
    wherein the product is as a methyl ethyl ketone replacement or acetone replacement.

11. The solvent composition of claim 1, wherein the solvent composition is a low toxicity solvent composition.

12. A product, comprising:
    the solvent composition of claim 1;
    wherein the product is a paint, varnish, fiberglass material, gelcoat, paint remover, varnish remover, coating, ink, adhesive, hard surface cleaner, household dye, tint, insecticide, laundry starch, lubricating grease, lubricating oil, automotive chemical, marker, nail polish, nail polish remover, shoe polish, undercoat, waterproofing compound, particleboard, surface preparation, general degreaser, heavy duty degreaser, laboratory wipe solvent, equipment wipe solvent, general purpose surface wipe cleaner, paint gun cleaner, paint line cleaner.

13. A product, comprising:
    the solvent composition of claim 2 wherein the product is a component in dissolution and processing of acrylic polymers; the production of resins; formulation or removal of nail polish; fiberglass manufacturing, gelcoat manufacturing; or waterproofing compounds.

14. The solvent composition of claim 13 wherein the resins are acrylic resins, urethane resins, alkyd resins, phenolic resins, polyaspartic urethane resins, epoxy resins, saturated or unsaturated polyester resins.

15. The solvent composition of claim 13 wherein the nail polish is a nitrocellulose-based nail polish, methacrylated monomer-based nail polish, oligonucleotide ("ligomer")-based nail polish, a UV cure nail polish or a LED cure nail polish.

16. A kit comprising the solvent composition of claim 1 together with instructions for use as a MEK replacement.

17. The solvent composition of claim 1 consisting of:
(a) methyl acetate in an amount of about 72% v/v;
(b) dimethyl carbonate in an amount of about 20% v/v; and
(c) benzyl alcohol in an amount of about 8% v/v.

* * * * *